(12) United States Patent
Matthews

(10) Patent No.: US 8,191,398 B1
(45) Date of Patent: Jun. 5, 2012

(54) VAPOR GENERATOR SAFETY RELEASE DEVICE

(75) Inventor: Robin L. Matthews, Port Deposit, MO (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 300 days.

(21) Appl. No.: 12/559,603

(22) Filed: Sep. 15, 2009

(51) Int. Cl.
*G01N 21/00* (2006.01)
(52) U.S. Cl. .................................................... 73/1.03
(58) Field of Classification Search .................. None
See application file for complete search history.

(56) References Cited

U.S. PATENT DOCUMENTS

| | | | | | |
|---|---|---|---|---|---|
| 2,143,585 | A | * | 1/1939 | Stein | 99/293 |
| 3,760,773 | A | * | 9/1973 | Christensen | 122/4 R |
| 4,027,791 | A | * | 6/1977 | Samuels | 222/396 |
| 4,567,748 | A | * | 2/1986 | Klass et al. | 73/1.05 |
| 5,728,927 | A | * | 3/1998 | Ong | 73/1.06 |
| 2008/0060408 | A1 | * | 3/2008 | Guth et al. | 73/1.03 |

* cited by examiner

*Primary Examiner* — Robert R Raevis
(74) *Attorney, Agent, or Firm* — Ulysses John Biffoni

(57) ABSTRACT

A vapor generator safety relief device for use in a surety system includes a conical flask, manifold, bubbler, and relief valve. The manifold includes a first chamber for inlet gas and a second chamber for outlet gas. The first chamber comprises an inlet port, an inlet tube, and a relief valve housing. The second chamber comprises an outlet tube and an outlet port. The bubbler is confluent with the inlet tube and disposed within the flask.

4 Claims, 2 Drawing Sheets

VAPOR GENERATOR SAFETY RELEASE DEVICE

GOVERNMENTAL INTEREST

The invention described herein may be manufactured, used and licensed by or for the U.S. Government.

TECHNICAL FIELD

This invention relates to the field of chemical agent vapor generator systems which are used for calibrating and testing detectors, respirators, and other equipment.

BACKGROUND

The present invention pertains generally to the field of chemical agent vapor generator systems which are used for specialized purposes. Such purposes include calibrating and testing chemical agent detectors, challenging protective respirators such as gas masks with a controlled concentration of chemical agent to determine respirator protection factors, and similar applications involving toxic chemicals. These systems typically utilize chemical warfare agents such as Tabun (GA), Sarin (GB), Soman (GD), Cyclosarin (GF), Lewisite (L), Sulfur mustard gas (HD, H, HT, HL, HQ), Nitrogen mustard gas (HN1, HN2, HN3), and V-Agents (VE, VG, VM, VR, VX). In addition to such chemical warfare agents, these vapor generator systems may be used with toxic industrial chemicals and toxic industrial materials. The present invention comprises a safety release device for preventing the possible over-pressurization of such systems, which could cause component failure and the uncontrolled release of toxic chemicals. For the purposes herein, the phrase "surety system" will be used to refer to any system designed to operate with chemical warfare agents, toxic industrial chemicals, toxic industrial materials, or any combination thereof.

A chemical agent vapor generator system that would benefit from the present invention is described in U.S. Pat. No. 5,728,927, which is incorporated herein by reference. The system of the '927 patent provides a means for creating a conditioned chemical agent airstream through the blending of a chemical agent airstream with a controlled relative humidity airstream. The '927 system, however, relies on a traditional flask bubbler with a rubber stopper to generate the controlled relative humidity airstream. Over-pressurization within this system, as well as other similar vapor generator systems, can occur because of a downstream blockage of gas flow, an excess inlet flow rate, or other causes. Such over-pressurization can result in a component failure and the uncontrolled release of toxic chemicals. For example, the rubber stopper of the traditional flask bubbler can be forced out of the flask if the pressure is too great thus resulting in an uncontrolled release of gas or the uncontrolled dispersion of broken glass. While it is possible to include pressure relief valves as components within chemical agent vapor generator systems either upstream or downstream of the flask bubbler, or both upstream and downstream, there are limitations to this approach. Even with such precautions of including one or more pressure relief valves within the system it is still possible that the local pressure at the flask bubbler could exceed the safe working pressure of the flask bubbler if, for example, a flow blockage occurred between the flask bubbler and the relief valve. In addition, for such surety systems, minimizing the number of components is desirable because of the exposure of these components to toxic chemicals and the corresponding need for decontamination and special handling.

The present invention overcomes these problems by providing a vapor generator with combined bubbler and pressure relief means and a limited number of parts which are easy to clean and decontaminate.

SUMMARY

A safety relief device for use in a surety system is described. The device includes a conical flask, manifold, bubbler, and relief valve. The manifold includes a first chamber for inlet gas and a second chamber for outlet gas. The first chamber includes an inlet port, an inlet tube, and a pressure relief valve housing. The second chamber includes an outlet tube and an outlet port. The bubbler is confluent with the inlet tube and disposed within the flask.

Aspects of the invention may include one or more of the following. The conical flask may be made of glass. Additionally, the entire manifold may be made of glass, including the inlet and outlet ports, inlet and outlet tubes, bubbler, relief valve housing, and relief valve port. The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the drawings indicate like elements.

DETAILED DESCRIPTION

Figure 1:
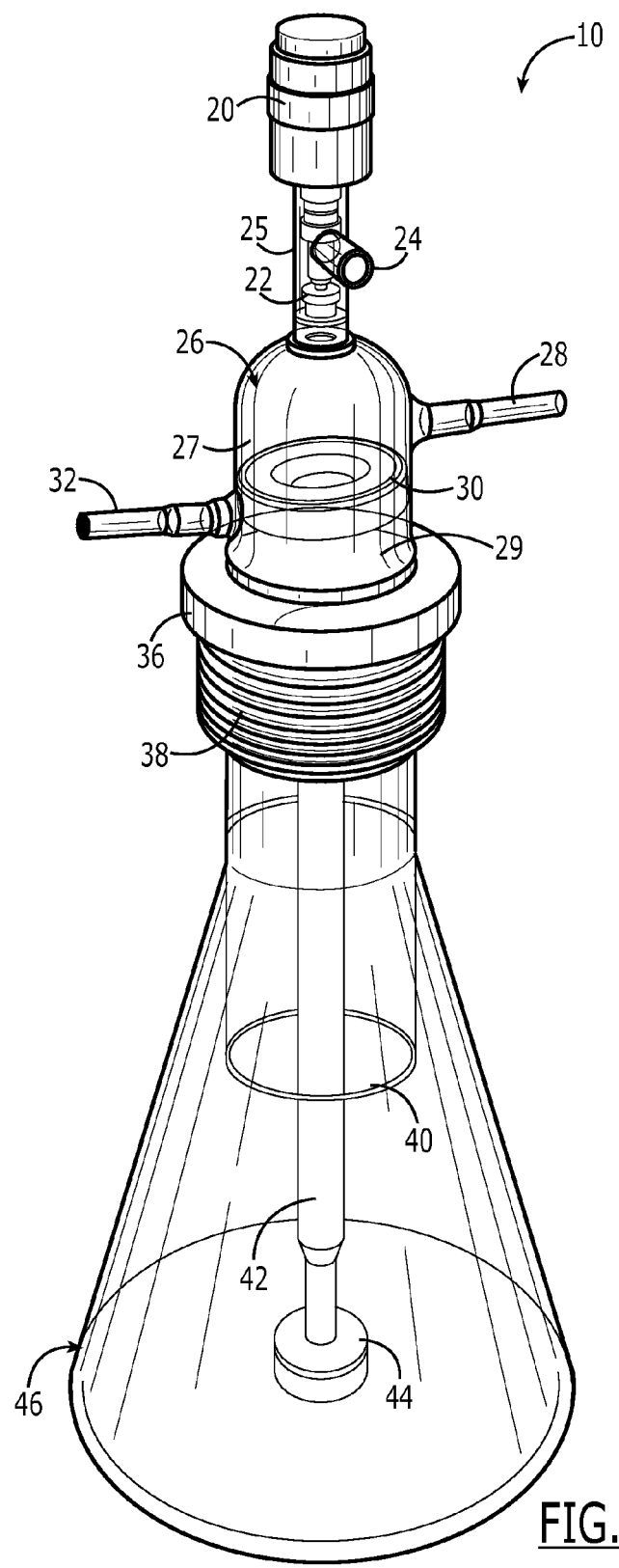
FIG. 1 is a perspective view of vapor generator safety relief device according to the teachings of the present invention.

A vapor generator safety relief device 10 for use in a surety system is shown in FIG. 1. In the preferred embodiment illustrated here, flask 46 is a conical flask, preferably made of glass, and having a threaded neck for engaging flask cap 36. Flask 46 serves as a vessel for holding a liquid, such as water or a chemical agent, and for housing the lower portion of manifold 26, which includes inlet tube 42, bubbler 44, and outlet tube 40. Flask 46 may be made of borosilicate glass, also known under the trade name PYREX, or it may be made of another type of glass used for laboratory glassware.

Manifold 26 is held in place relative to flask 46 by flask cap 36. The substantially cylindrical body of the lower portion of manifold 26 fits within the cylindrical interior of flask cap 36 which in turn is attached to flask 46 via a threaded connection. That is, flask cap 36 includes external threads 38 which engage corresponding internal threads on the neck of flask 46. The body of flask cap 36 contains a cylindrical bore or hole which is of an internal diameter only slightly larger than the outer diameter of outlet tube 40, thus providing a snug fit of manifold 26 when disposed within the bore of flask cap 36. An o-ring 52 (shown in FIG. 2) is used to provide a gas-tight seal between flask cap 36, manifold 26, and flask 46, thus preventing gas from flowing out of the flask through any path other than outlet port 32 or pressure relief port 24. Flask cap 36 is preferably made of plastic, such as nylon or polytetrafluoroethylene (PTFE) which is known by the brand name TEFLON. O-ring 52 is preferably made of synthetic rubber such as butyl or nitrile.

The upper portion of manifold 26, which is visible above flask cap 36, includes inlet port 28, outlet port 32, and relief valve port 24. Manifold 26 also includes outlet tube 40, inlet tube 42, and bubbler 44. Bubbler 44 in the preferred embodiment is a sintered glass disc. This allows manifold 26 to be constructed entirely of glass which provides transparency, an easily cleaned component, and compatibility with surety system laboratory practices. Borosilicate glass, also known under the trade name PYREX, may be used as the material choice given its overall properties which include a low coefficient of thermal expansion.

Manifold 26 also includes separation wall 30 which divides manifold 26 into a first chamber 27 for inlet gas and a second chamber 29 for outlet gas. The relief valve housing 25 and relief valve port 24 are part of first chamber 26 in the preferred embodiment as illustrated. Thus first chamber 26 provides for the confluence, or flowing together, of gas within inlet port 28, inlet tube 42, and relief valve housing 25. Similarly, second chamber 29 provides for the confluence of gas within outlet port 32 and outlet tube 40.

In normal operation, inlet gas is channeled by first chamber 27 as follows. Gas flowing into inlet port 28 flows through inlet tube 42 and bubbler 44 where it bubbles into the liquid within flask 46. Outlet gas is channeled by second chamber 29 as follows. Gas above the liquid surface in flask 46 is able to flow out into and through outlet tube 40 and continue flowing through outlet port 32 where it goes to other parts of the chemical agent vapor generator system. Separation wall 30, which divides first chamber 27 and second chamber 29, prevents gas from outlet tube 40 from flowing to first chamber 27 and inlet port 28.

The top of manifold 26, which is part of first chamber 27, includes a housing 25 for relief valve 22 and relief port 24. Relief valve 22 is preferably made of plastic such as TEFLON. Spring adjustment cap 20 holds relief valve 22 within valve housing 25 of manifold 26 and, at normal operating pressures, is seated such that gas cannot flow out of relief port 24. Spring adjustment cap 20 is adjustably biased to provide a suitable range of pressures at which the seal is broken to allow gas to flow out of relief port 24 thereby relieving any undesired pressure in the system. Such bias is typically set to a value within 5 to 50 psi. Further details of the relief valve are provided below in reference to the exploded view of FIG. 2.

When device 10 is in use it is typically placed within a laboratory fume hood or on a laboratory bench. The surface area provided by the base of conical flask 46, combined with the weight and center of gravity of the fluid contained within flask 46, serves to stabilize device 10 so it is self-standing and stable. In use, device 10 is connected to a source of gas (not shown), such as air or nitrogen, by connecting a tube from the gas source to inlet port 28. Typically, the source is a pressurized gas cylinder or air compressor and a regulator is used between the source and inlet port 28 in order to lower and regulate the gas pressure as delivered to device 10. The gas source as delivered to device 10 is thereby at a higher pressure than the gas in device 10 which causes a continuous flow of gas into inlet 28 and the first chamber 27 of manifold 26 where it flows down towards and into flask 46 through inlet tube 42 until it bubbles out of bubbler 44 and into the liquid held in flask 46. Gas above the liquid level within flask 46 is free to flow up through outlet tube 40 of the second chamber 29 and continues flowing through outlet port 32. Separation wall 30, which divides the first chamber 27 and the second chamber 29, channels the gas within outlet tube 40 so that it can only exit via outlet port 32.

The safety release feature of the present invention functions as follows. If the pressure within device 10 exceeds a pre-established set point, the force resulting from gas pressure acting against relief valve 22 will cause spring 60 (shown in FIG. 2) to compress thereby breaking the gas seal of relief valve 22 and allowing gas to escape through relief port 24. Relief port 24 can be connected to an appropriate exhaust filter, such as activated carbon, so that any released toxic gasses can be contained and filtered.

Figure 2:
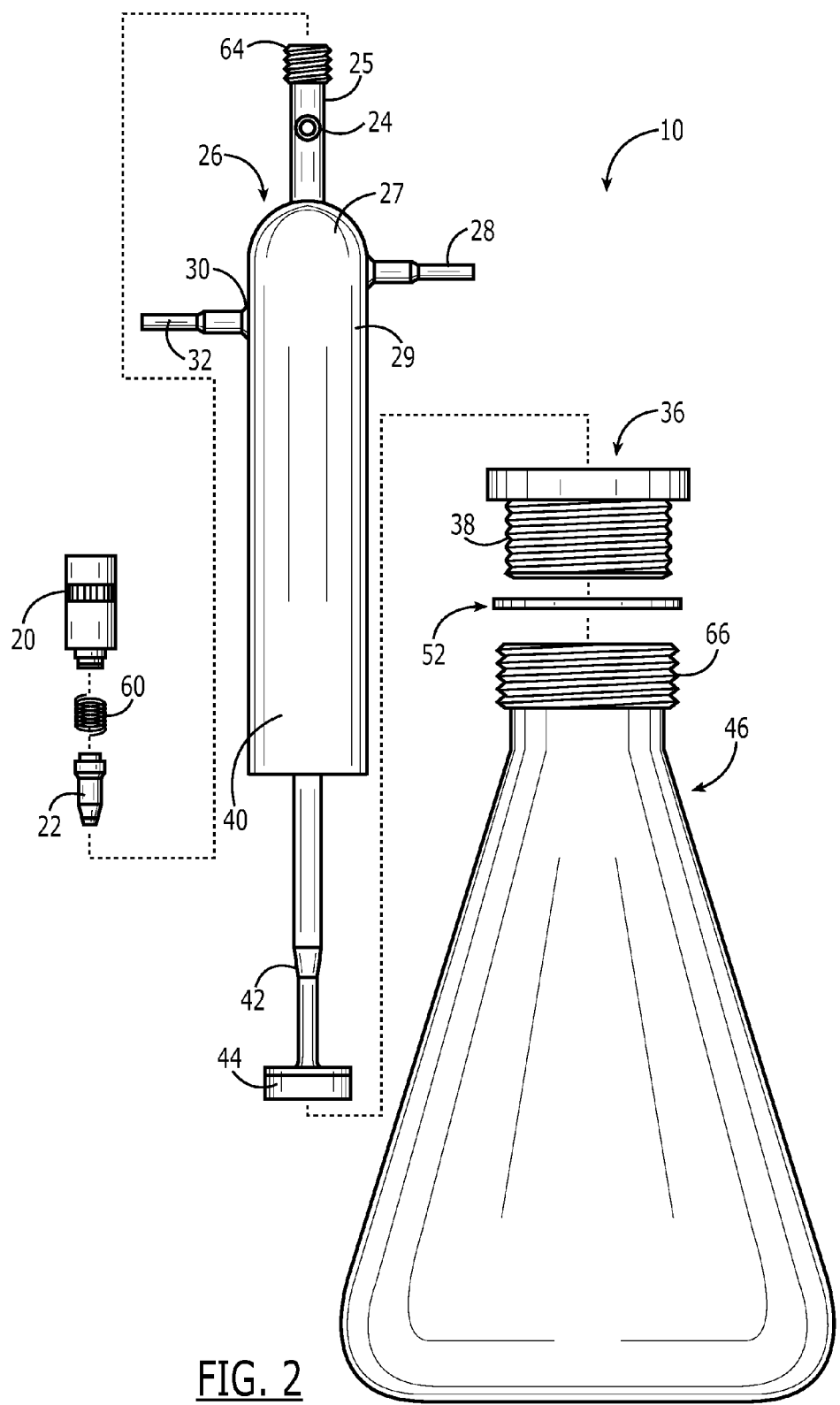
FIG. 2 is an exploded view of a vapor generator safety relief device according to the teachings of the present invention.

Turning to the exploded view of FIG. 2, further details of the present invention are described. Relief valve 22 is attached to relief valve adjustment cap 20 by spring 60 which serves to bias relief valve 22 against the valve seat in relief valve housing 25. Spring adjustment cap 20 contains internal threads to adjustably engage external threads 64 of manifold 26. Turning relief valve adjustment cap 20 clockwise causes spring 60 to be further compressed, therefore establishing a higher set point at which pressure relief valve 22 will lift out of its seat and allow gas to flow out of relief port 24 of manifold 26. Turning relief valve adjustment cap 20 counterclockwise causes spring 60 to be relaxed, therefore establishing a lower set point at which pressure relief valve 22 will lift out of its seat and allow gas to flow out of relief port 24 of manifold 26.

The all-glass construction of the preferred embodiment of manifold 26 is readily apparent in FIG. 2. The upper portion of manifold 26 includes inlet port 28, outlet port 32, and relief port 24. The upper portion of manifold 26 also includes relief valve housing 25 and external threads 64 for engaging the corresponding internal thread of relief valve adjustment cap 20. The lower portion of manifold 26 includes inlet tube 42, bubbler 44, and outlet tube 40. As noted above, all of these parts of manifold 26 are made of glass which provides flow visibility and is easy to clean and decontaminate. Additionally, the bubbler and relief valve functions are provided using a minimal number of parts.

Flask cap 36 includes external threads 38 for engaging internal threads 66 of flask 46. The interior bore of flask cap 36 is sized to allow manifold 26 to fit snuggly within flask cap 36. In particular, the outer diameter of outlet tube 40 of manifold 26 is only slightly smaller than the inner diameter of the interior bore of flask cap 36, thus providing a snug fit when manifold 26 is inserted into the bore of flask cap 36. O-ring 52 is sized to fit snuggly around outlet tube 40 of manifold 26. It is placed around outlet tube 40 of manifold 26 after inserting manifold 26 into flask cap 36 and before threading flask cap 36 into threaded flask neck 66, thereby forming a gas-tight seal once flask cap 36 is fully threaded into flask neck 66.

While specific embodiments of the invention have been described, it will be understood that additional embodiments and various modifications may be made without departing from the spirit and scope of the invention. For example, manifold 26 may vary in shape and size while still performing the functions as described herein. Accordingly, these and other embodiments of the invention fall within the scope of the following claims.

What is claimed is:

1. A vapor generator safety relief device for use in a surety system comprising:
   a conical flask having a base and a threaded neck;
   a manifold having a first chamber for inlet gas and a second chamber for outlet gas, said manifold having an inlet port, an inlet tube, and a relief valve housing in fluid connection with said first chamber, and said manifold having an outlet tube and an outlet port in fluid connection with said second chamber;
   a flask cap for fastening said manifold to said conical flask;
   a bubbler confluent with said inlet tube and disposed within said conical glass flask;
   a relief valve cap; and a relief valve contained within said relief valve housing by said relief valve cap.

2. A vapor generator safety relief device for use in a surety system as recited in claim 1 wherein said conical flask is made of glass.

3. A vapor generator safety relief device for use in a surety system as recited in claim 2 wherein said manifold is made of glass.

4. A vapor generator safety relief device for use in a surety system as recited in claim 3 wherein said relief valve cap includes means for adjustably biasing said relief valve contained within said relief valve housing.

* * * * *